(12) United States Patent
Presura et al.

(10) Patent No.: US 8,185,189 B2
(45) Date of Patent: May 22, 2012

(54) INVESTIGATION OF BODY STRUCTURES

(75) Inventors: Cristian Presura, Eindhoven (NL); Maarten Van Herpen, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 1204 days.

(21) Appl. No.: 11/721,468

(22) PCT Filed: Dec. 15, 2005

(86) PCT No.: PCT/IB2005/054261
§ 371 (c)(1),
(2), (4) Date: Jun. 12, 2007

(87) PCT Pub. No.: WO2006/067699
PCT Pub. Date: Jun. 29, 2006

(65) Prior Publication Data
US 2009/0292202 A1    Nov. 26, 2009

(30) Foreign Application Priority Data
Dec. 20, 2004  (EP) .................................... 04300924

(51) Int. Cl.
*A61B 8/00*  (2006.01)
*A61B 6/00*  (2006.01)

(52) U.S. Cl. ................. 600/476; 600/437; 606/3; 606/9; 606/15

(58) Field of Classification Search .................. 600/407, 600/437, 443, 458, 476, 573; 606/6, 9, 15
See application file for complete search history.

(56) References Cited

U.S. PATENT DOCUMENTS

| | | | |
|---|---|---|---|
| 5,085,080 A | 2/1992 | Yu | |
| 6,322,557 B1* | 11/2001 | Nikolaevich et al. | 606/6 |
| 6,405,069 B1 | 6/2002 | Oraevsky et al. | |
| 6,466,806 B1 | 10/2002 | Geva et al. | |
| 6,498,942 B1 | 12/2002 | Esenaliev et al. | |
| 6,901,087 B1* | 5/2005 | Richardson et al. | 372/20 |
| 7,063,694 B2* | 6/2006 | Nahen et al. | 606/15 |
| 2002/0169394 A1* | 11/2002 | Eppstein et al. | 600/573 |
| 2003/0167002 A1 | 9/2003 | Nagar et al. | |
| 2003/0225320 A1 | 12/2003 | Jeon et al. | |
| 2004/0054268 A1 | 3/2004 | Esenaliev et al. | |
| 2005/0119643 A1* | 6/2005 | Sobol et al. | 606/9 |
| 2006/0084959 A1* | 4/2006 | Davenport et al. | 606/15 |

FOREIGN PATENT DOCUMENTS
WO          03039364          5/2003

* cited by examiner

*Primary Examiner* — Tse Chen
*Assistant Examiner* — Baisakhi Roy

(57) ABSTRACT

A pulsed radiation beam is directed toward a body structure having a configuration or physical characteristic that changes over time, the radiation being pulsed at a pulse modulation frequency. A detector detects acoustic oscillations set up in the body resultant from the incident pulsed radiation and produces an output signal representative of one or more parameters of the acoustic oscillations. A control system controls operation of the radiation delivery and a processor to process the detector output signal. The pulse modulation frequency of the pulsed radiation is changed over a predetermined range of modulation frequencies and the processor determines the structure resonant frequency from the detector output.

10 Claims, 1 Drawing Sheet

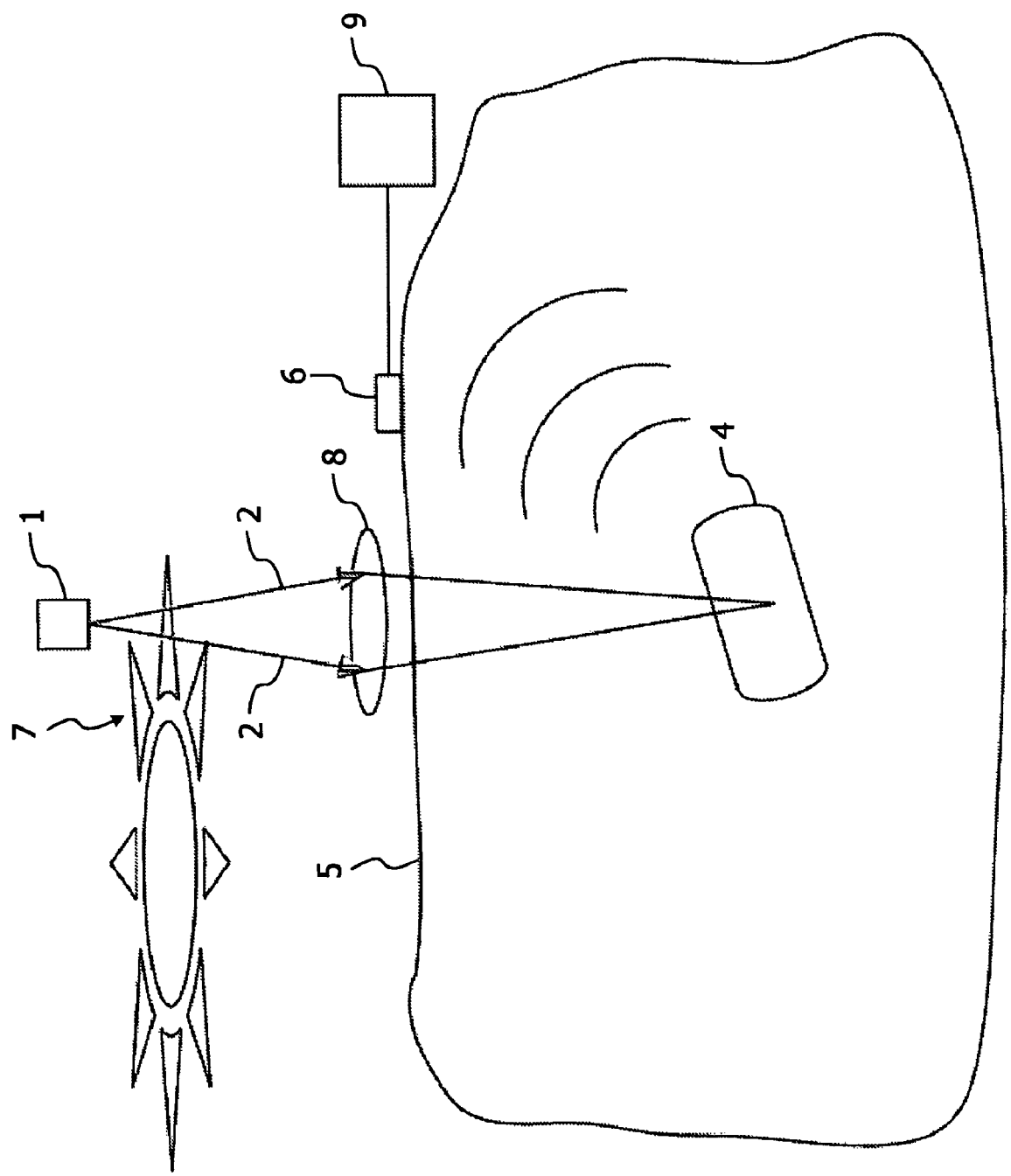

INVESTIGATION OF BODY STRUCTURES

The present invention relates to investigation of body structures and particularly soft structures of the human or animal body.

The invention is particularly applicable to photo-acoustic investigative techniques such as photo-acoustic imaging as used, for example for analysis of blood and blood vessels.

Photo-acoustic imaging is based on the principle of thermal expansion. Light radiation, typically from a laser, is directed from a source and absorbed in a restricted volume of tissue and that consequently undergoes thermal expansion and relaxation. The rise in temperature generates an acoustic transient, which propagates through the tissue to the surface. For short laser pulses, e.g. ~12 ns, the pressure is linearly proportional to the absorbed energy density. At the tissue surface, sensitive acoustic detectors, for example piezoelectric detectors, detect the acoustical amplitude, and the interior structure of the body can be reconstructed by using the acoustic transit times, enabling an image of the structure to be rendered. In general the detector output is proportional to the absorbed optical energy.

If a whole volume is scanned, the technique can provide even a 3d image of the blood vessels. The wavelength of the laser is chosen such, that a strong absorption in the blood vessels will occur, and therefore the light is absorbed in the blood of the blood vessels and that leads to a high degree of thermal expansion and relaxation.

A problem occurs in instances where the absorption coefficient of the structure under investigation is small and/or for example the structure is deep within a surrounding tissue such as the dermis, up to 10 mm. In order to address this problem it is possible to use an acoustic resonance effect to enhance the acoustic signal, by pulsing the incident light radiation beam at a pulse modulation frequency that matches the resonance frequency of the structure. This may be achieved for example by chopping the incident continuous-wave light at the resonance frequency or by providing a light source that produces pulses at the structure resonance frequency. The acoustic resonance effect enhances operability of the technique.

By absorbing the light coming from the laser, the temperature of the blood increases locally, creating for a short time a sound wave in the tissue. If the repetition frequency of the light matches the resonance frequency of the blood vessel, the sound wave will be greatly amplified by resonance. This in turn will significantly increase the signal that reaches the acoustic sensor. A photo-acoustic technique using a resonance technique is disclosed in U.S. Pat. No. 6,466,806.

An improved technique has now been devised.

According to a first aspect, the present invention provides apparatus for investigation of a body structure having a configuration or physical characteristic that changes over time, the apparatus comprising:
   a radiation delivery arrangement arranged to direct pulsed radiation toward the body structure, wherein the radiation is pulsed at a pulse modulation frequency:
   a detector arrangement for detecting acoustic oscillations set up in the body resultant from the incident pulsed radiation and arranged to produce an output signal representative of one or more parameters of the acoustic oscillations;
   a control system arranged to control operation of the radiation delivery arrangement, the control system including a processor arranged to process the detector output signals;
   wherein the pulse modulation frequency of the pulsed radiation is changed over a predetermined range of modulation frequencies and the processor determines the structure resonant frequency from the detector output.

The radiation delivery arrangement is preferably controlled to emit radiation pulsed at a pulse modulation frequency matched to the structure resonant frequency determined by the processor.

In a preferred realisation, the structure resonant frequency varies over time and the control system alters the pulse modulation frequency to match the structure resonant frequency over time. The pulse modulation frequency is preferably continuously altered to match the altering structure resonant frequency over time.

The processor preferably determines the structure resonant frequencies at different times. It is preferred that the processor determines physical properties of the structure as a result of analysing the time difference resonant frequencies predicted for the structure.

The structure may vary cyclically and the pulse modulation frequencies may be matched to the resonant frequencies through the cycle. Monitoring of the variation of the pulse modulation frequency at different points in the cycle (or constantly through the cycle) will give a representation of physical changes of the body structure. for example where investigating a blood vessel, monitoring of the variation of the pulse modulation frequency at different points in the cycle (or constantly through the cycle) can give a representation of blood vessel flexibility, heart rate, blood pressure or other parameters).

According to a further aspect, the present invention provides a method of investigating a body structure having a configuration or physical characteristic that changes over time, the method comprising:
   directing pulsed radiation toward the body structure, wherein the radiation is pulsed at a pulse modulation frequency:
   detecting acoustic oscillations set up in the body resultant from the incident pulsed radiation and producing an output signal representative of one or more parameters of the acoustic oscillations;
   adjusting the pulse modulation frequency of the pulsed radiation is over a predetermined range of modulation frequencies, and
   from the detected acoustic oscillations determining the structure resonant frequency.

It is preferred that the pulsed radiation is controlled to emit radiation pulsed at a pulse modulation frequency matched to the determined structure resonant frequency.

According to a further aspect, the present invention provides a system enabling investigation of a body structure having a configuration or physical characteristic that changes over time, the system comprising means for determining the resonant frequency of the structure by analysing data representative of:
   output signals from a detector arrangement for detecting acoustic oscillations set up in the body or structure resultant from pulsed radiation directed toward the structure, and
   the variation of a pulse modulation frequency of the pulsed radiation over a predetermined range of modulation frequencies.

Beneficially, the pulse modulation frequency of the pulsed radiation is matched to the structure resonant frequency determined by the system. Desirably, the structure resonant frequencies at different times is determined. It is preferred that the system enables physical properties of the structure to be determined as a result of analysing the time difference resonant frequencies predicted for the structure.

The invention may be implemented and the system as defined may be implemented by way of a computer programme product.

The invention will now be further described by way of example only, with respect to the accompanying drawing which is a schematic representation of apparatus in accordance with the invention.

In the drawing is shown a simplified diagrammatic representation of apparatus and a system for use in accordance with the present invention.

A laser 1 directs a light beam 2 of a preselected wavelength toward a structure 4 in the form of a blood vessel embedded in surrounding living tissue 5. The wavelength of the light beam emitted from the laser 1 is typically selected to match a preferential absorption wavelength of the blood, blood component or the vessel. The light is absorbed in the blood of the blood vessels and that leads to thermal expansion and relaxation an creation of the photo-acoustic vibrations/oscillations. In the embodiment shown a lens 8 is present to focus the beam 2; such a lens may not be required in practice.

An acoustic detector 6 is orientated to detect acoustic oscillations/vibrations set up by the opt-acoustic interaction. The detector 6 may be a piezoelectric transducer arrangement, an optical detector arrangement or other.

The light beam 2 is pulsed at a modulated pulse frequency for reasons well explained herein. The frequency modulated light beam 2 can be provided in several ways. For example a beam chopper 7 may be employed to chop a continuous-wave laser beam. This is illustrated in the embodiment as shown in the drawing. The beam 2 is chopped into pulses by a rotary chopper 7 that periodically blocks the path of the laser beam 2.

Alternatively an acoustic-optical modulator (AOM) can be used to modulate a continuous-wave laser beam. This method will allow higher modulation frequencies than a conventional chopper and avoids the need for moving parts associated with a chopper arrangement. As a further alternative, a pulsed laser with variable repetition frequency may be employed. In any event, in accordance with the present invention, the control system for the apparatus enables the pulse repetition (modulation) frequency and/or the pulse duration must be variable in a controlled manner to a degree.

In accordance with the present invention, the pulse modulation frequency is matched to the natural frequency of the structure under investigation, in this instance the blood vessel. The resonance in the blood vessel can occur in two ways.

The blood vessel acts as an organ tube to promote the main resonance vibration. If a radial acoustical excitation of the tube is considered (which is the main resonance vibration), an estimate can be made of the first order resonance frequency by $f=v/D$, where $v=1402$ m/s is the velocity of sound in water, which will give a good estimate of the speed of sound in blood. For a D=100 mm blood vessel a resonant frequency of about 14 MHz, is obtained which is in the reach of an AOM.

Stretching and relaxing of the walls of the blood vessels also occur. When the blood vessel expands due to a change in blood-pressure (due to heart-beat), the radial acoustical resonance frequency (see above) of the blood vessel will change. This effect may be used to determine heartbeat frequency, blood pressure and flexibility of the blood vessel.

Next the frequency of the intensity modulation needs to be chosen. Because blood vessels with different diameters exist in the body, each vessel has a different resonance frequency. Therefore the modulation frequency of the light needs to be scanned over a certain frequency range, depending on the size of the blood vessels that need to be measured or imaged. Thus by tuning the pulse modulation frequency of the laser to the resonance frequency of the blood vessel an enhanced acoustic vibration of the vessel is obtained, due to resonance.

At the tissue surface, the detector 6 detects the acoustical amplitude and phase, and the interior structure can be reconstructed by using the acoustic transit times and phases, using a suitable processor 9. In general the detector output is proportional to the absorbed optical energy.

Using resonance enhanced acoustic imaging the signal is much stronger than in conventional acoustic imaging. It is also more specific, because the enhancement will only enhance the image of blood vessels (since only the blood vessels will resonate). Selection of the modulation light pulse repetition frequency by means of scanning over a certain frequency range, and monitoring the detector output to select the resonance targeted frequency is particularly advantageous.

The improved sensitivity may permit the measurement of the concentration of some particular molecules in the blood (such as i.e. glucose). This can be done by first adjusting the wavelength of the laser to the absorption of peak on the wanted molecule and then adjusting the modulation frequency to a frequency with a strong resonant signal. The intensity on the acoustic sensor will then measure the amount of absorption, which is correlated with the concentration of the molecule in the blood.

The stretching and relaxing of the blood vessels due to heartbeats will cause variations in the diameter of the vessels and will therefore change the acoustic resonance frequency in time. This effect can be used in a detector. The laser output is controlled (particularly by output from processor 9) to scan over a certain frequency range, and monitoring the detector output to select the resonance targeted frequency for different points in time (for example different points in a cardiac cycle).

By monitoring the change in resonance frequency due to heartbeat, it is possible to find the amount of stretching of the blood vessels. This gives information about the flexibility of the blood vessels. The acoustic resonance frequency may depend on the pressure in the blood vessel. In that case this invention can be used in a blood-pressure meter. Processing the detector signals for different points in time and for changing scanned light pulse modulation frequencies enables different measurements and observations to be made.

Various modifications may be proposed. For instance, it is not necessary to focus the beam, because the resonance signal is enhanced. Imaging can be performed, by placing more acoustic sensors at different locations and processing signals appropriately to render an image at a display. Measuring heartbeat, blood pressure and concentration levels in the blood can be done with a single sensor at the skin tissue.

It should be noted that the above-mentioned embodiment illustrates rather than limits the invention, and that those skilled in the art will be capable of designing many alternative embodiments without departing from the scope of the invention as defined by the appended claims. In the claims, any reference signs placed in parentheses shall not be construed as limiting the claims. The word "comprising" and "comprises", and the like, does not exclude the presence of elements or steps other than those listed in any claim or the specification as a whole. The singular reference of an element does not exclude the plural reference of such elements and vice-versa. Aspects of the invention may be implemented by means of hardware comprising several distinct elements, and by means of a suitably programmed computer. In a device claim enumerating several means, several of these means may be embodied by one and the same item of hardware. The mere fact that certain measures are recited in mutually different dependent claims does not indicate that a combination of these measures cannot be used to advantage.

The invention claimed is:

1. An apparatus for investigation of a body structure having a configuration or physical characteristic that changes over time, the apparatus comprising:
   a radiation delivery arrangement arranged to direct pulsed radiation toward the body structure, wherein the radiation is pulsed at a pulse modulation frequency:
   a detector arrangement for detecting acoustic oscillations set up in the body resultant from the incident pulsed radiation and arranged to produce an output signal representative of one or more parameters of the acoustic oscillations;
   a control system arranged to control operation of the radiation delivery arrangement, the control system including a processor arranged to process the detector output signals;
   wherein the pulse modulation frequency of the pulsed radiation is changed over a predetermined range of modulation frequencies and the processor determines a structure resonant frequency of the body structure from the detector output signals, and
   wherein the pulsed radiation is of a preselected spectral wavelength profile matching an absorption characteristic of the body structure or a medium related to the body structure, and
   wherein the processor further determines the structure resonant frequency as a result of analyzing a time difference between the detected acoustic oscillations and resonant frequencies predicted for the body structure.

2. The apparatus according to claim 1, wherein the radiation delivery arrangement is controlled to emit radiation pulsed at a pulse modulation frequency matched to the structure resonant frequency determined by the processor.

3. The apparatus according to claim 1, wherein the structure resonant frequency varies over time and the control system alters the pulse modulation frequency to match the structure resonant frequency over time.

4. The apparatus according to claim 1, wherein the pulsed radiation is laser radiation.

5. The apparatus according to claim 1, wherein the pulsed radiation is in the form of a pulsed directed beam.

6. The apparatus according to claim 1, wherein the detector arrangement includes a piezoelectric transducer.

7. The apparatus according to claim 1, wherein the detector arrangement comprises an optical detector arrangement.

8. The apparatus according to claim 1, wherein the radiation delivery arrangement and detector arrangement enable data to be captured from a line, section area or volume and the processor includes image rendering means for processing the detector arrangement data and enabling rendering of an image on a display.

9. A method of investigating a body structure having a configuration or physical characteristic that changes over time, the method comprising the acts of:
   directing pulsed radiation toward the body structure, wherein the radiation is pulsed at a pulse modulation frequency:
   detecting acoustic oscillations set up in the body resultant from the incident pulsed radiation and producing an output signal representative of one or more parameters of the acoustic oscillations;
   matching a preselected spectral wavelength profile of the pulsed radiation to an absorption characteristic of the body structure or a medium related to the body structure;
   adjusting the pulse modulation frequency of the pulsed radiation is over a predetermined range of modulation frequencies; and
   from analyzing a time difference between the detected acoustic oscillations and resonant frequencies predicted for the body structure, determining a structure resonant frequency of the body structure.

10. A system enabling investigation of a body structure having a configuration or physical characteristic that changes over time, the system comprising means for determining resonant frequency of the body structure by analyzing data representative of:
   output signals from a detector arrangement for detecting acoustic oscillations set up in the body structure resultant from pulsed radiation directed toward the body structure, and
   the variation of a pulse modulation frequency of the pulsed radiation over a predetermined range of modulation frequencies,
   wherein the pulsed modulation frequency is of a preselected spectral wavelength profile matching an absorption characteristic of the body structure or a medium related to the body structure, and
   wherein the means for determining determines the resonant frequency as a result of analyzing a time difference between the detected acoustic oscillations and resonant frequencies predicted for the structure.

* * * * *